(12) United States Patent
Mauler-Machnik et al.

(10) Patent No.: US 7,795,178 B2
(45) Date of Patent: Sep. 14, 2010

(54) FUNGICIDAL ACTIVE COMBINATIONS SPIROXAMINE, PROTHIOCONAZOLE AND TEBUCONAZOLE

(75) Inventors: Astrid Mauler-Machnik, Leichlingen (DE); Friedrich Kerz-Möhlendick, Leverkusen (DE); Stefan Dutzmann, Langenfeld (DE); Peter Dahmen, Neuss (DE)

(73) Assignee: Bayer CropScience AG, Monheim (DE)

( * ) Notice: Subject to any disclaimer, the term of this patent is extended or adjusted under 35 U.S.C. 154(b) by 188 days.

(21) Appl. No.: 10/576,181

(22) PCT Filed: Oct. 19, 2004

(86) PCT No.: PCT/EP2004/011800

§ 371 (c)(1),
(2), (4) Date: Jul. 26, 2006

(87) PCT Pub. No.: WO2005/039294

PCT Pub. Date: May 6, 2005

(65) Prior Publication Data

US 2007/0066669 A1    Mar. 22, 2007

(30) Foreign Application Priority Data

Oct. 23, 2003 (DE) .................... 103 49 503

(51) Int. Cl.
*A01N 25/00* (2006.01)
*A01N 63/00* (2006.01)

(52) U.S. Cl. .................... 504/116.1; 504/118

(58) Field of Classification Search .......... 504/116.1, 504/118
See application file for complete search history.

(56) References Cited

U.S. PATENT DOCUMENTS

| 4,532,341 A | 7/1985 | Holmwood et al. ......... 549/559 |
| 4,626,595 A | 12/1986 | Holmwood et al. ......... 549/559 |
| 4,723,984 A | 2/1988 | Holmwood et al. ............ 71/76 |
| 4,789,672 A | 12/1988 | Holmwood et al. ......... 514/184 |
| 4,851,405 A | 7/1989 | Krámer et al. .............. 514/212 |
| 4,871,390 A | 10/1989 | Holmwood et al. ............ 71/92 |
| 4,897,107 A | 1/1990 | Holmwood et al. ............ 71/92 |
| 4,904,298 A | 2/1990 | Holmwood et al. ............ 71/92 |
| 4,911,746 A | 3/1990 | Holmwood et al. ............ 71/92 |
| 5,397,795 A * | 3/1995 | Valcke ....................... 514/383 |
| 5,789,430 A * | 8/1998 | Jautelat et al. .............. 514/384 |
| 5,859,039 A | 1/1999 | Jautelat et al. .............. 514/384 |
| 6,503,932 B2 * | 1/2003 | Eicken et al. ............... 514/355 |
| 6,884,798 B2 * | 4/2005 | Baron et al. ................ 424/761 |

FOREIGN PATENT DOCUMENTS

| EP | 0 393 746 A1 | 10/1990 |
| EP | 0 627 163 A1 | 12/1994 |
| WO | 96/38040 A1 | 12/1996 |
| WO | 96/41533 A1 | 12/1996 |
| WO | 98/47367 A1 | 10/1998 |
| WO | 01/37666 | 5/2001 |

OTHER PUBLICATIONS

Latteur et al., Effects of 20 fungicides on the infertility of conidia of the aphid entomopathogenic fungus *Erynia neoaphidis*, BioControl, 47:435-444, 2002.*
Pesticide Manual, 11th edition, (month unavailable) 1997, Editor: C.D.S. Tomlin, p. 1144-1146, Tubuconazole.
Weeds, 15, (month unavailable) 1967, S.R. Colby, p. 20-22, "Calculating Synergistic and Antagonistic Responses of Herbicide Combinations".

* cited by examiner

*Primary Examiner*—Johann R. Richter
*Assistant Examiner*—Kristie L Brooks
(74) *Attorney, Agent, or Firm*—Richard E. L. Henderson

(57) ABSTRACT

The present invention relates to a novel active compound combination that is highly suitable for controlling phytopathogenic fungi which contains the known 8-tert-butyl-1,4-dioxaspiro[4.5]decan-2-ylmethyl(ethyl)(propyl)amine (spiroxamine) and other known active compounds.

6 Claims, No Drawings

FUNGICIDAL ACTIVE COMBINATIONS SPIROXAMINE, PROTHIOCONAZOLE AND TEBUCONAZOLE

The present patent application has been filed under 35 U.S.C. 371 as a national stage application of PCT/EP2004/011800, filed Oct. 19, 2004, which was published in German as International Patent Publication WO 2005/039294 on May 6, 2005, and is entitled to the right of priority of German Patent Application 103 49 503.7, filed Oct. 23, 2003.

The present invention relates to an active compound combination comprising the known 8-tert-butyl-1,4-dioxaspiro[4.5]decan-2-ylmethyl(ethyl)(propyl)amine (spiroxamine) and further known active compounds, which combination is highly suitable for controlling phytopathogenic fungi.

It is already known that 8-tert-butyl-1,4-dioxaspiro[4.5]decan-2-ylmethyl(ethyl)(propyl)amine (spiroxamine) has fungicidal properties (cf. EP-A-0 281 842). The activity of this compound is good; however, at low application rates, it is sometimes unsatisfactory.

Furthermore, it is already known that numerous azole derivatives can be used for controlling fungi (cf. Pesticide Manual, 11th Edition (1997), page 1144; WO 96/16048). However, at low application rates, the activity of these compounds is likewise unsatisfactory.

It has now been found that an active compound combination comprising 8-tert-butyl-1,4-dioxa-spiro[4.5]decan-2-ylmethyl(ethyl)(propyl)amine (spiroxamine) (reference: EP-A 0 281 842) of the formula (I)

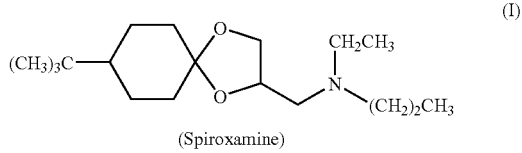

(Spiroxamine)

and (1) the compound of the formula (II) (reference: WO 96/16048)

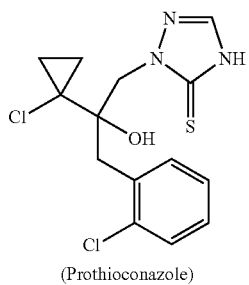

(Prothioconazole)

and (2) the compound of the formula (III) (reference: EP-A-0 040 345)

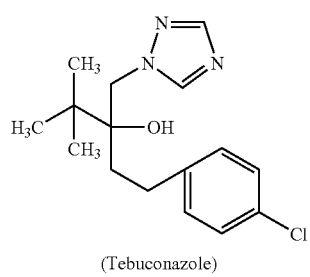

(Tebuconazole)

has very good fungicidal properties.

Surprisingly, the fungicidal activity of the active compound combination according to the invention comprising the three active compounds is considerably higher than the sum of the activities of the individual active compounds or the activity of the prior-art mixtures comprising in each case two active compounds. Thus, an unforeseeable true synergistic effect is present, and not just an addition of activities.

The active compound of the formula (I) is known (cf., for example, EP-A-0 281 842). The active compounds of the formulae (II) and (III) present in the active compound combination according to the invention in addition to the active compound of the formula (I) are likewise known (cf. references).

The following active compound combination is also known:

Active compound combination comprising compounds of the formulae (II) and (III): WO 98/47367.

If the active compounds in the active compound combination according to the invention are present in certain weight ratios, the synergistic effect is particularly pronounced. However, the weight ratios of the active compounds in the active compound combination can be varied within a relatively wide range.

In general, 0.1-10 parts by weight, preferably 0.2-5 parts by weight, of active compound of the formula (II), and 0.05-10 parts by weight, preferably 0.1-5 parts by weight, of active compound of the formula (III)

are present per part by weight of active compound of the formula (I).

The active compound combination according to the invention, applied simultaneously, that is jointly or separately, has very good fungicidal properties and can be employed for controlling phytopathogenic fungi, such as Plasmodiophoromycetes, Oomycetes, Chytridiomycetes, Zygomycetes, Ascomycetes, Basidiomycetes and Deuteromycetes.

The active compound combination according to the invention is particularly suitable for controlling cereal diseases, such as *Erysiphe, Cochliobolus, Pyrenophora, Rhynchosporium, Septoria, Fusarium, Pseudocercosporella* and *Leptosphaeria, Puccinia, Ustilago, Tilletia* and *Urocystis* and for controlling fungal infections in non-cereal crops such as vine, fruit, groundnut, vegetables, for example Phythophthora, *Plasmopara, Pythium*, powdery mildew fungi, such as, for example, *Sphaerotheca* or *Uncinula*, and causative organisms of leaf spot, such as *Venturia, Alternaria* and *Septoria* and also *Rhizoctonia, Botrytis, Sclerotinia* and *Sclerotium*.

The fact that the active compound combination is well tolerated by plants at the concentrations required for controlling plant diseases permits the treatment of above-ground parts of plants, of propagation stock and seeds, and of the soil. The active compound combination according to the invention can also be employed for foliar application or else as seed dressings.

The active compound combination according to the invention is also suitable for increasing the harvest yield. Moreover, it has reduced toxicity and is tolerated well by plants.

According to the invention, it is possible to treat all plants and parts of plants. Plants are to be understood here as meaning all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including the plant cultivars which can or cannot be protected by plant breeders' certificates. Parts of plants are to be understood as meaning all above-ground and below-ground parts and organs of plants, such as shoot, leaf, flower and root, examples which may be mentioned being leaves, needles, stems, trunks, flowers, fruit-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compounds is carried out directly or by activity on their environment, habitat or storage area according to customary treatment methods, for example by dipping, spraying, evaporating, atomizing, broadcasting, brushing-on and, in the case of propagation material, in particular in the case of seeds, furthermore by one- or multi-layer coating.

The active compound combination according to the invention can be converted to the customary formulations, such as solutions, emulsions, suspensions, powders, foams, pastes, granules, aerosols and microencapsulations in polymeric substances and in coating compositions for seeds, and ULV formulations.

These formulations are produced in a known manner, for example by mixing the active compounds or active compound combinations with extenders, that is liquid solvents, liquefied gases under pressure, and/or solid carriers, optionally with the use of surfactants, that is emulsifiers and/or dispersants, and/or foam formers. If the extender used is water, it is also possible to use, for example, organic solvents as auxiliary solvents. Essentially, suitable liquid solvents include: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, or else water. Liquefied gaseous extenders or carriers are to be understood as meaning liquids which are gaseous at ambient temperature and under atmospheric pressure, for example aerosol propellants such as butane, propane, nitrogen and carbon dioxide. Suitable solid carriers are: for example ground natural minerals such as kaolins, clays, talc, chalk, quartz, attapulgite, montmorillonite or diatomaceous earth, and ground synthetic minerals such as finely divided silica, alumina and silicates. Suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, corn cobs and tobacco stalks. Suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, or else protein hydrolyzates. Suitable dispersants are: for example lignosulfite waste liquors and methylcellulose.

Tackifiers such as carboxymethylcellulose and natural and synthetic polymers in the form of powders, granules or latices, such as gum arabic, polyvinyl alcohol and polyvinyl acetate or else natural phospholipids such as cephalins and lecithins and synthetic phospholipids can be used in the formulations. Other additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compounds, preferably between 0.5 and 90%.

The active compound combination according to the invention, as such or in its formulations, can also be applied in a mixture with other known fungicides, bactericides, acaricides, nematicides or insecticides—in particular when treating seed—, to broaden the activity spectrum or to prevent the development of resistance, for example.

A mixture with other known active compounds such as herbicides or with fertilizers and growth regulators is also possible.

The compounds (I), (II) and (III) can be applied simultaneously, that is jointly or separately, or in succession, the sequence, in the case of separate application, generally not having any effect on the control results.

The active compound combination can be used as such, in the form of its formulations or as the use forms prepared therefrom, such as ready-to-use solutions, emulsifiable concentrates, emulsions, suspensions, wettable powders, soluble powders and granules. They are used in the customary manner, for example by watering, spraying, atomizing, scattering, spreading, and as a powder for dry seed treatment, a solution for seed treatment, a water-soluble powder for seed treatment, a water-soluble powder for slurry treatment, or by encrusting.

When using the active compound combination according to the invention, the application rates can be varied within a relatively wide range, depending on the kind of application. In the treatment of parts of plants, the application rates of active compound combination are generally between 0.1 and 10 000 g/ha, preferably between 10 and 1000 g/ha. In the treatment of seeds, the application rates of active compound combination are generally between 0.001 and 50 g per kilogram of seed, preferably between 0.01 and 10 g per kilogram of seed. In the treatment of the soil, the application rates of active compound combination are generally between 0.1 and 10 000 g/ha, preferably between 1 and 5000 g/ha.

The good fungicidal activity of the active compound combination according to the invention is evident from the examples below. While the individual active compounds exhibit weaknesses with regard to fungicidal activity, the combinations made up of three active compounds have an activity which exceeds the sum of individual activities.

A synergistic effect in fungicides is always present when the fungicidal activity of the active compound combination is greater than the sum of the activities of the active compounds applied individually.

The expected activity for a given combination of 2 or 3 active compounds can be calculated in accordance with S. R. Colby ("Calculating Synergistic and Antagonistic Responses of Herbicide Combinations", Weeds 1967, 15, 20-22) as follows:

If

X denotes the efficacy when using active compound A at an application rate of m g/ha, Y denotes the efficacy when using active compound B at an application rate of n g/ha, Z denotes the efficacy when using active compound C at an application rate of r g/ha, $E_1$ denotes the efficacy when using active compounds A and B at application rates of m and n g/ha, and $E_2$ denotes the efficacy when using active compounds A and B and C at application rates of m and n and r g/ha, then $$E_1 = X + Y - \frac{X \cdot Y}{100}$$

and for a combination of 3 active compounds:

$$E_2 = X + Y + Z - \frac{X \cdot Y + X \cdot Z + Y \cdot Z}{100} + \frac{X \cdot Y \cdot Z}{10000}$$

The efficacy here is determined in %. 0% denotes an efficacy which corresponds to that of the control, while an efficacy of 100% means that no infection is observed.

If the actual fungicidal activity is greater than that calculated, then the activity of the combination is superadditive: in other words, a synergistic effect is obtained. In this case the efficacy actually observed must be greater than the value calculated using the above-indicated formula for the expected efficacies $E_1$ and $E_2$, respectively.

The invention is illustrated by the example below. The invention is not, however, limited to the example.

EXAMPLES

Example 1

*Erysiphe* Test (Wheat)/Protective

To produce a suitable preparation of active compound, a commercial formulation of active compound or active compound combination is diluted with water to the desired concentration.

To test for protective activity, young plants are sprayed with the active compound preparation at the stated application rate.

After the spray coating has dried on, the plants are dusted with spores of *Erysiphe graminis* f.sp.tritici.

The plants are placed in a greenhouse at a temperature of about 20° C. and a relative atmospheric humidity of about 80% to promote the development of mildew pustules.

Evaluation is carried out 6 days after the inoculation. 0% means an efficacy which corresponds to that of the control, whereas an efficacy of 100% means that no infection is observed.

The active compound combination according to the invention has very good fungicidal properties.

TABLE 1

*Erysiphe* test (wheat)/protective

| Active compound | Active compound application rate in g/ha | Efficacy in % |
|---|---|---|
| known: | | |
| (I) spiroxamine | 125 | 33 |
| (II) prothioconazole | 125 | 78 |
| (III) tebuconazole | 125 | 78 |
| according to the invention: | | |
| (I) + (II) + (III) 1:0.64:0.64 | 55 + 35 + 35 | 100 |

Example 2

*Leptosphaeria nodorum* Test (Wheat)/Curative

To produce a suitable preparation of active compound, a commercial formulation of active compound or active compound combination is diluted with water to the desired concentration.

To test for curative activity, young plants are sprayed with a conidia suspension of *Leptosphaeria nodorum*. The plants remain in an incubation cabin at 20° C. and 100% relative atmospheric humidity for 48 hours and are then sprayed with the active compound preparation at the stated application rate.

The plants are placed in a greenhouse at a temperature of about 15° C. and a relative atmospheric humidity of about 80%.

Evaluation is carried out 12 days after the inoculation. 0% means an efficacy which corresponds to that of the control, whereas an efficacy of 100% means that no infection is observed.

The active compound combination according to the invention has very good fungicidal properties.

TABLE 2

*Leptosphaeria nodorum* test (wheat)/curative

| Active compound | Active compound application rate in g/ha | Efficacy in % |
|---|---|---|
| known: | | |
| (I) spiroxamine | 500 | 0 |
| (II) prothioconazole | 500 | 20 |
| (III) tebuconazole | 500 | 40 |
| according to the invention: | | |
| (I) + (II) + (III) 1:0.24:0.24 | 340 + 80 + 80 | 60 |

Example 3

*Fusarium nivale* (var. *majus*) Test (Wheat)/Curative

To produce a suitable preparation of active compound, a commercial formulation of active compound or active compound combination is diluted with water to the desired concentration.

To test for curative activity, young plants are sprayed with a conidia suspension of *Fusarium nivale* var. *majus*. The plants remain in an incubation cabin at 15° C. and 100% relative atmospheric humidity for 24 hours and are then sprayed with the active compound preparation at the stated application rate.

After the spray coating has dried on, the plants remain in a greenhouse under transparent incubation hoods at a temperature of about 15° C. and a relative atmospheric humidity of about 100%.

Evaluation is carried out 11 days after the inoculation. 0% means an efficacy which corresponds to that of the control, whereas an efficacy of 100% means that no infection is observed.

The active compound combination according to the invention has very good fungicidal properties.

TABLE 3

*Fusarium nivale* (var. majus) test (wheat)/curative

| Active compound | Active compound application rate in g/ha | Efficacy in % found* | calc.** |
|---|---|---|---|
| known: | | | |
| (I) spiroxamine | 140 | 17 | |
| (II) prothioconazole | 55 | 17 | |
| (III) tebuconazole | 55 | 33 | |
| according to the invention: | | | |
| (I) + (II) + (III) 1:0.4:0.4 | 140 + 55 + 55 | 100 | 54 |

*found = activity found
**calc. = activity calculated using Colby's formula

The invention claimed is:

1. An active compound combination consisting essentially of a compound of formula (I)

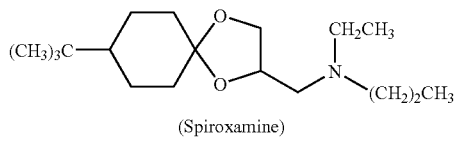

(Spiroxamine)

and (1) a compound of formula (II)

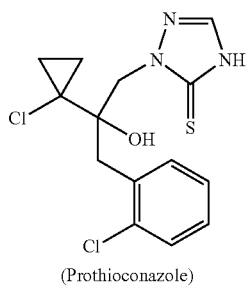

(Prothioconazole)

wherein the weight ratio of the compound of formula (I) to the compound of formula (II) is from 1:0.1 to 1:10, and (2) a compound of formula (III)

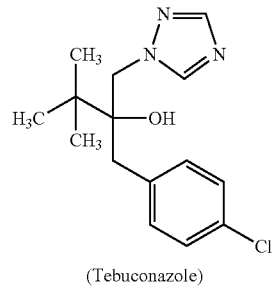

(Tebuconazole)

wherein the weight ratio of the compound of formula (I) to the compound of formula (III) is from 1:0.05 to 1:10.

2. A method of controlling fungi comprising allowing an effective amount of an active compound combination as defined in claim 1 to act on the fungi and/or their habitat, plants, parts of plants, seeds, soils, areas, materials, or spaces to be kept free from the fungi.

3. The method as claimed in claim 2 comprising applying the compound of formula (I), the compound of formula (II), and the compound of formula (III) simultaneously together or separately or in succession.

4. A propagation material treated by the method of claim 2.

5. A fungicidal composition comprising an active compound combination according to claim 1 and one or more extenders and/or surfactants.

6. A process for preparing a fungicidal composition comprising mixing an active compound combination as claimed in claim 1 with one or more extenders and/or surfactants.

* * * * *